United States Patent
Neuroth et al.

(10) Patent No.: US 6,797,174 B2
(45) Date of Patent: Sep. 28, 2004

(54) CONNECTING SYSTEM FOR PLASTIC COLUMNS

(75) Inventors: Willi Neuroth, Rossdorf (DE); Günter Sättler, Reinheim (DE); Klaus Kreher, Muenster (DE)

(73) Assignee: Merck Patent GmbH, Darmstadt (DE)

( * ) Notice: Subject to any disclaimer, the term of this patent is extended or adjusted under 35 U.S.C. 154(b) by 66 days.

(21) Appl. No.: 10/332,489

(22) PCT Filed: Jun. 13, 2001

(86) PCT No.: PCT/EP01/06677

§ 371 (c)(1),
(2), (4) Date: Jan. 9, 2003

(87) PCT Pub. No.: WO02/06818

PCT Pub. Date: Jan. 24, 2002

(65) Prior Publication Data

US 2003/0150883 A1 Aug. 14, 2003

(30) Foreign Application Priority Data

Jul. 13, 2000 (DE) .......................... 100 34 076

(51) Int. Cl.⁷ .............................................. B01D 15/08
(52) U.S. Cl. .................................... 210/656; 210/198.2
(58) Field of Search .................. 210/635, 656, 210/659, 198.2, 502.1; 95/82, 88; 96/101, 106

(56) References Cited

U.S. PATENT DOCUMENTS

| 4,026,803 A | * | 5/1977 | Abrahams et al. ........ 210/198.2 |
| 4,806,238 A | * | 2/1989 | Sattler et al. ............ 210/198.2 |
| 5,863,428 A | * | 1/1999 | Ma et al. ................. 210/198.2 |
| 6,372,142 B1 | * | 4/2002 | Gjerde et al. ............... 210/635 |
| 6,576,133 B2 | * | 6/2003 | Gjerde et al. ............... 210/635 |

FOREIGN PATENT DOCUMENTS

| DE | 8614805 | * | 1/1988 |
| DE | 4112258 | * | 10/1992 |
| DE | 19726164 | * | 12/1998 |

* cited by examiner

Primary Examiner—Ernest G. Therkorn
(74) Attorney, Agent, or Firm—Millen, White, Zelano & Branigan, P.C.

(57) ABSTRACT

The invention relates to a plastic cartridge system including a cartridge having a plastic-covered column, said column including a monolithic sorbent and at least one closing cap which is applied to the ends of the column. The cartridge also includes a connecting system having at least one divided supporting screw which is held in position by a closing cap or a spacer ring, and at least one end piece which can be screwed onto a supporting screw in order to connect an elution agent inlet and an elution agent outlet.

9 Claims, 1 Drawing Sheet

CONNECTING SYSTEM FOR PLASTIC COLUMNS

REFERENCE TO RELATED APPLICATIONS

This application is a 371 of PCT/EO01/06677 filed Jun. 13, 2001.

The invention relates to a cartridge system which is especially matched to the properties of plastic-clad monolithic chromatography columns.

Columns for chromatography, in particular for HPLC, usually have a cladding of metal or plastic into which the sorbent has been introduced. Besides conventional particulate sorbents, monolithic sorbents, as disclosed, for example, in WO 94/19687 and in WO 95/03256, are also gaining increased importance.

In order to produce columns with particulate sorbents, column tubes, typically of metal or plastic, are sealed at one end with a filter system and filled with the sorbent under pressure. During this operation, it is ensured that the sorbent particles fill the entire tube in order that no dead space is formed which could impair the separation efficiency. After filling, the column is sealed at both ends with integrated or attached filter systems in order that sorbent cannot escape during use. The connection to eluent feed and discharge takes place through screw connections, which are screwed directly onto the column (for plastic or metal columns) or via re-usable cartridge systems which are inserted into the columns (for metal columns).

In contrast to particulate sorbents, which can be introduced into prefabricated metal columns, some peculiarities have to be taken into account in the cladding and connection of monolithic sorbents: Monolithic sorbents are generally removed from the mould after production and re-clad for use. Since monolithic sorbents have a rigid shape and dead spaces arising during the cladding cannot be compensated for, the cladding of the monoliths must be carried out with no dead space and in a pressure-stable manner. It has been found that plastic cladding is particularly suitable since it has adequate pressure stability and can be applied to the monolithic sorbent with no dead space. The sorbent generally terminates flush with the cladding at the ends.

Monolithic columns have hitherto been connected to the eluent feed or outlet via screw connections, which are screwed directly onto a thread cut into the plastic cladding. If the screw connection is removed, the monolithic sorbent is directly accessible and can easily be damaged. A connecting system for monolithic plastic-clad sorbents in the form of a cartridge system was hitherto unknown. Owing to the material properties of sorbent and cladding, the metal cartridge systems known for particulate sorbents cannot be applied to monolithic plastic-clad sorbents. In particular, different demands are made of column termination elements, such as, for example, filter elements.

The object of the present invention was therefore to develop a connecting system for plastic-clad monolithic sorbents which enables use as a cartridge system.

It has been found that a cartridge system consisting of a column with cap which is installed directly on the ends of the cladding, a spacer ring for integration of a pre-column, a divided supporting screw and an end piece which can be screwed onto the supporting screw for the connection of eluent feed and discharge meets all requirements of a connecting system for columns comprising plastic-clad monolithic sorbents.

The present invention therefore relates to a cartridge system at least comprising a cartridge consisting of a plastic-clad column with monolithic sorbent on which a cap is installed at least at one end, and a plastic connecting system consisting of at least one divided supporting screw and at least one end piece which is screwed onto the said supporting screw for the connection of eluent feed and discharge.

In a preferred embodiment, a device is present which enables the supporting screw to be placed against the cartridge at at least two different defined points. This device can be, for example, at least one spacer ring or a shape (for example recess or bead) provided for this purpose in the cap.

In a particularly preferred embodiment, the device is at least one spacer ring.

In a preferred embodiment, the cartridge cap has an internal thread for screwing onto the column.

The present invention also relates to the use of the cartridge system according to the invention for the chromatographic separation of at least two substances.

DESCRIPTION OF THE PREFERRED EMBODIMENTS

Figure 1:
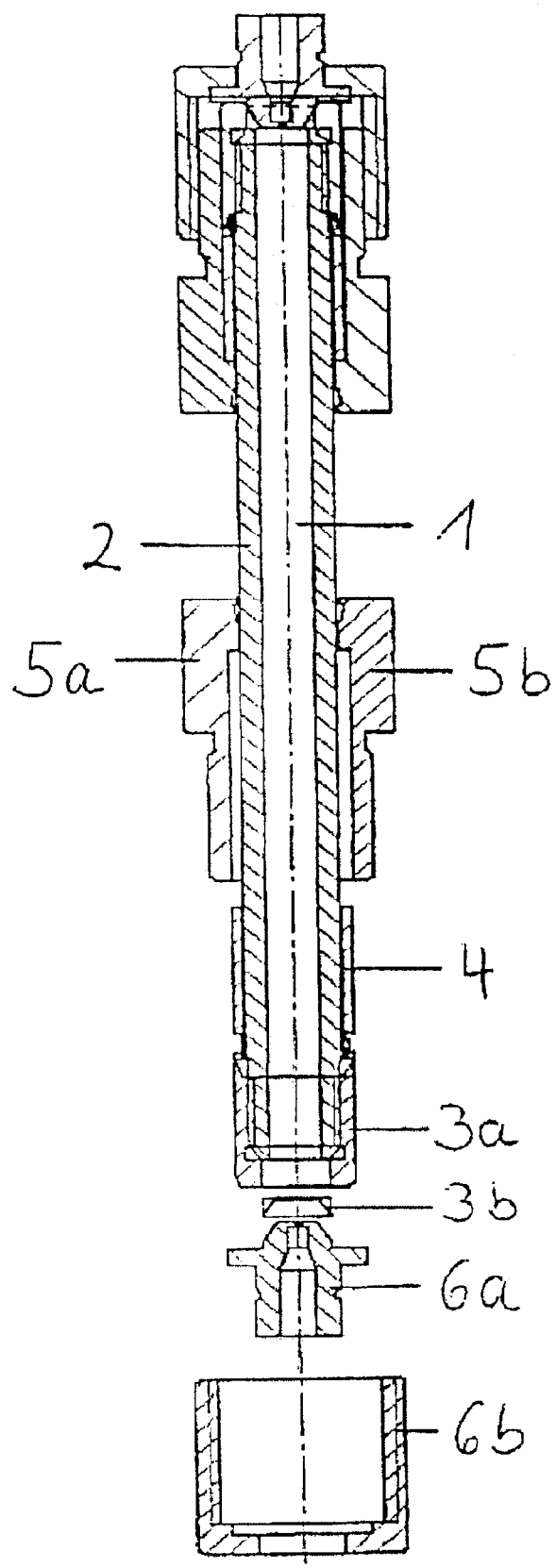
FIG. 1 shows a cartridge system according to the invention having a cartridge and the connecting system.

The cartridge system according to the invention consists of a cartridge, which in turn consists at least of a column with cap and a connecting system. The cartridge system is suitable for plastic-clad columns with monolithic sorbents, irrespective of the nature of the sorbent or of the plastic. The columns are preferably those with inorganic monolithic sorbents which are clad with thermoplastics, such as, for example, polyaryls, polyether ketones, polyesters, aromatic polyamides, polyimides, polybenzimidazoles, preferably fluorinated polymers, polyphenylene sulfides, polyether sulfones or liquid-crystalline polymers (LCPs) and mixtures of two or more of these materials. If the plastics do not exhibit adequate pressure stability or are difficult to process, they may have been treated with stabilisers, such as fibre materials, inorganic materials, or pigments, for example chalk, talc, mica or inorganic oxides, such as silicon dioxide. The cartridge system according to the invention is particularly suitable for columns comprising fibre-reinforced plastics, especially comprising glass or in particular carbon fibre-reinforced PEEK (polyether ether ketone). The other constituents of the cartridge system, such as the cap, supporting screw and end pieces, likewise preferably consist of plastic, where the same materials can generally be employed as are also used for the cladding. It is also possible to employ fibre-reinforced plastics for these parts, since they have greater mechanical stability. However, non-fibre-reinforced plastics are usually also sufficiently stable for parts such as the cap, spacer ring, supporting screw and end piece.

For protection of the monolithic sorbent and for homogeneous distribution of the eluent on the sorbent, the column is firstly provided, in accordance with the invention, with a cap. This cap can be permanently or reversibly connected to the column, i.e. it can be attached, for example, by screwing, adhesive bonding, clamping or welding. It has been found that the attachment known for metal columns via a groove into which two half-shells can be inserted (for example disclosed in EP 0268185) cannot be used in the case of plastic columns. The plastic material is destabilised to a very considerable extent by cutting-in of a groove and thus loses the requisite pressure stability. The cap is preferably attached by screwing onto a thread located directly on the cladding. This offers the possibility of integrating even columns which are provided with a conventional screwed-on connecting system into the cartridge system according to the invention.

In columns for the cartridge system according to the invention, the monolithic sorbent preferably terminates flush with the cladding. In this case, the cap serves as sorbent protection. It furthermore contains a passage through which eluent can reach the column. This passage typically consists of a distribution system, such as a perforated plate, a frit or a filter, which ensures uniform distribution of the eluent on the sorbent, and a sealing element, which prevents the occurrence of dead spaces or the escape of eluent at the side.

If the sorbent does not terminate flush with the cladding, but instead a distribution element is already integrated into the column cladding at the ends, it is not necessary for a second distribution element to be integrated into the cap. In this case, a liquid passage is sufficient. Furthermore, it must be ensured that any dead spaces are compensated for by correspondingly shaped sealing elements.

The cap can consist of a workpiece with integrated passage, etc., or can be composed of a plurality of parts. For example, the cap can have a passage into which a distribution unit is inserted.

A divided supporting screw is attached to the cap according to the invention. The position of the supporting screw is determined by the shape and dimensions of the cap and any device provided for this purpose. An end piece with connection for eluent feed and discharge is then screwed onto the thread of the divided supporting screw. The end piece can consist of one or more parts. The construction of end pieces is known to the person skilled in the art from other connecting systems. In general, it has, for the connection of eluent feed and discharge, an internal thread into which a capillary or line can be screwed.

In order to enable integration of a pre-column, the position of the end piece must be variable in such a way that on the one hand a pre-column can be inserted between the cap and end piece and on the other hand the end piece can be joined to the cap directly in an accurately fitting manner. Since the position of the cap cannot be changed, this is achieved in accordance with the invention by sliding the supporting screw.

In one embodiment, the cap is shaped in such a way that the supporting screw can be placed in two different positions. For example, the cap can have a device intended for this purpose in the form of one or two grooves. The corresponding supporting screw has on the inside, for example, a raised ring, which can be placed against the end of the cap or against a groove. If a pre-column is to be integrated, the groove located closer to the column end is selected, so that the supporting screw projects beyond the end of the column and a pre-column can be installed. If no pre-column is provided, the supporting screw is placed against the rear groove or against the end of the cap, so that the end piece can be screwed on in an accurately fitting manner.

In a preferred embodiment, the cap does not have grooves. Instead, at least one loose spacer ring which surrounds the column jacket and can be moved freely thereon between the caps at the ends of the column is located beneath the cap as device for positioning the supporting screw. If integration of a pre-column is not intended, the spacer ring is moved right up against the cap. The supporting screw has on the inside a raised ring, a shoulder or another stop means. This is placed against the spacer ring so that the supporting screw is positioned in such a way that the end piece is positioned against the cap in an accurately fitting manner. For integration of a pre-column, the spacer ring is slid away from the cap, so that the supporting screw is located directly against the cap. This creates space for the installation of a pre-column. In accordance with the invention, provision may be made for one spacer ring, which is positioned in each case against the cap to which a pre-column is to be connected, two spacer rings, i.e. one for each side, or alternatively a plurality of spacer rings of various thickness for the installation of pre-columns of various length.

In a further embodiment, the spacer ring is shaped in such a way that it can be joined to the cap in two ways. If a pre-column is not required, the spacer ring is joined to the cap in such a way that a cavity is not created between the cap and end piece on attachment of the supporting screw. For installation of a pre-column, the position of the spacer ring is changed in such a way that a cavity is created. For example, the spacer ring is in this embodiment designed in such a way that it has at least two cut-outs in the length of the pre-column, i.e., for example, a toothed end, on the side facing towards the cap. The cap is correspondingly shaped in such a way that the spacer ring can be installed either with the outer edge or, through rotation, snaps into the cut-outs and can thus be moved closer to the cap.

FIG. 1 shows a cartridge system according to the invention having a cartridge in a connecting system. At the upper end, all parts of the system are attached to the column or cartridge; in the lower part, they are, for better clarity, shown coordinated loosely to the column. The cap (3) consists of two parts, a threaded part (3a) with passage, which is screwed onto the column, consisting of sorbent (1) and cladding (2). A distribution element (3b) is placed against the threaded part. The spacer ring (4) is connected to the cap (3) via a locking mechanism, such as, for example, a snap-in mechanism. If it is not required, the lock can be released and the spacer ring slid away to the column centre. For use without pre-column, as shown in FIG. 1, the divided supporting screw (5a, 5b) is placed against the spacer ring (4). This is carried out via a shoulder provided in the lower part of the supporting screw. For connection of eluent feed and discharge, the end piece (6) is screwed onto the supporting screw (5a, 5b). The end piece (6) consists of two parts, the connector (6a) and a union nut (6b).

The cartridge system according to the invention thus offers a simple system for the connection of plastic columns with monolithic sorbents. The cap means that it is not necessary to integrate a filter unit directly into the column. Protection of the monolithic sorbent against damage and uniform feed of the eluent onto the sorbent are provided by the cap. The attachment of the cap is matched to the plastic cladding.

The connection between end piece and cap is provided via a divided supporting screw. Metal screws which have been cut and later divided give rise to the problem that the thread only functions reliably if the screw parts originally belonging together are used together. This is unsuitable for mass production. In the case of divided screws made from plastic, this problem does not exist if they are made, in accordance with the invention, as two defined parts, preferably by means of injection moulding. In this way, exchangeability of the thread halves is ensured.

Since the cap is preferably screwed onto the column, means must be provided, for integration of a pre-column, for positioning of the supporting screw in at least two possible positions. This is facilitated in accordance with the invention by a device provided for this purpose, preferably by a spacer ring.

The system according to the invention can be utilised as cartridge system by, for example, using the column with caps and, if desired, with spacer ring as a replaceable cartridge. In general, a column for chromatographic operation is provided at both ends with the cap and the connections according to the invention.

Even without further details, it is assumed that a person skilled in the art will be able to utilise the above description in its broadest scope. The preferred embodiments and examples should therefore merely be regarded as descriptive disclosure which is absolutely not limiting in any way.

The complete disclosure content of all applications, patents and publications mentioned above and below, in particular of the corresponding application DE 100 34 076, filed on 13 Jul. 2000, is incorporated into this application by way of reference.

What is claimed is:

1. A cartridge system comprising at least
   a cartridge comprising a plastic-clad column with monolithic sorbent on which a cap is installed at least at one end, and
   a plastic connecting system comprising at least one divided supporting screw and at least one end piece which is screwed onto the said supporting screw for the connection of eluent feed and discharge.

2. A cartridge system according to claim 1, further comprising a device allowing at least one of the at least one supporting screw to be placed against the cartridge at least at two different points.

3. A cartridge system according to claim 2, wherein the device is at least one spacer ring.

4. A cartridge system according to claim 2, wherein the device is a recess or bead in the cap.

5. A cartridge system according to claim 1, further comprising an internal thread on the cartridge cup.

6. A cartridge system according to claim 1, wherein the sorbent is inorganic.

7. A cartridge system according to claim 1, wherein the plastic is a thermoplastic.

8. A cartridge system according to claim 1, wherein the plastic is fiber reinforced.

9. A method of chromatographic separation of at least two-substances comprising passing the at least two substances through a cartridge system according to claim 1.

* * * * *

UNITED STATES PATENT AND TRADEMARK OFFICE
CERTIFICATE OF CORRECTION

PATENT NO. : 6,797,174 B2
DATED : September 28, 2004
INVENTOR(S) : Neuroth et al.

It is certified that error appears in the above-identified patent and that said Letters Patent is hereby corrected as shown below:

<u>Column 6,</u>
Line 15, change "cup" to -- cap --

Signed and Sealed this

Third Day of May, 2005

JON W. DUDAS
*Director of the United States Patent and Trademark Office*